United States Patent [19]

Recsei

[11] Patent Number: 5,011,772

[45] Date of Patent: Apr. 30, 1991

[54] HIGH YIELD PROTEIN PRODUCTION SYSTEM

[75] Inventor: Paul A. Recsei, New York, N.Y.

[73] Assignee: Public Health Research Institute of the City of N.Y., New York, N.Y.

[21] Appl. No.: 152,635

[22] Filed: Feb. 5, 1988

[51] Int. Cl.$^5$ .................. C12P 21/00; C12P 21/02; C12N 15/00

[52] U.S. Cl. .................. 435/69.1; 435/69.2; 435/69.52; 435/320.1; 935/48

[58] Field of Search .................. 435/68, 70, 71, 91, 435/172.1, 172.3, 252.3, 252.31–252.35, 320, 69.1, 71.2, 71.1, 69.52, 69.2; 536/27; 935/11, 48, 72, 73, 74

[56] References Cited

PUBLICATIONS

Recsei et al.; Proc. Natl. Acad. Sci. U.S.A., 84:1127, (1987).
Heinrich et al.; Mol. Gen. Genet., 209:563, (1987).

*Primary Examiner*—James Martinell
*Attorney, Agent, or Firm*—White & Case

[57] ABSTRACT

Recombinant vectors and a method for producing a predetermined protein in a trademark microbial host are provided. The recombinant vectors are autonomously replicable expression vectors for use in *B. subtilis* and *E. coli* and express proteins therein. The vectors contain DNA sequences which code for preprolysostaphin protein secretion sequences which are necessary and sufficient for efficient secretion of the predetermined protein by transformed hosts. A gene for a predetermined protein is inserted into the vectors such that the order of genes in the vector is 5'-vector DNA-preprolysostaphin protein secretion sequence-predetermined protein sequence-vector DNA-3'. Optionally and preferably, the vectors also contain additional DNA sequences coding for staphylococcal nuclease which is a secretable detectable protein tag. A gene for a predetermined protein is inserted into such vectors such that the order of genes in the vector is 5'-vector DNA-preprolysostaphin protein secretion sequence-predetermined protein sequence-nuclease tag sequence-vector DNA-3'.

34 Claims, 5 Drawing Sheets

X: 5'—CC TCG AGG GGA TCC CC|GG GGA TCC TCT AGA G.TC—3'
      Ser Arg Gly Ser       Gly Ser Ser Arg Val

Y: 5'—CC TCG AGG GGA TCC ACC C|G GGT GGA TCC TCT AGA GTC—3'
      Ser Arg Gly Ser Thr      Gly Gly Ser Ser Arg Val

Z: 5'—CC TCG AGG GGA TCC CCC|GGG GGA TCC TCT AGA GTC—3'
      Ser Arg Gly Ser Pro    Gly Gly Ser Ser Arg Val

HIGH YIELD PROTEIN PRODUCTION SYSTEM

BACKGROUND OF THE INVENTION

The present invention relates to a method and recombinant vectors for producing a predetermined protein which can be secreted in large amounts from a transformed microorganism. The protein so produced is a fusion protein containing an N-terminal secretion sequence derived from preprolysostaphin which is cleaved from the final product by normal processing mechanisms of the host. The invention also relates to an optional method of tagging such fusion proteins such that the transformed microorganism producing the predetermined protein of interest can be readily identified.

Well-established gene cloning techniques have allowed a wide variety of proteins to be expressed in microbial hosts. A major problem with current prokaryotic protein expression systems, which is a significant impediment to the production of commercially useful amounts of specific proteins by biotechnology techniques, is the inability of the transformed microorganism to secrete the cloned gene product (i.e., protein) into the medium in significant quantities.

Transport of proteins through membranes is a highly complex process common to all cellular organisms. The amino terminal portion of the precursors of proteins destined for secretion (i.e., preproteins) is usually a largely hydrophobic amino acid sequence called the signal peptide or signal sequence. Such sequences have been found in preproteins destined for secretion synthesized by both eukaryotes, including yeasts, and prokaryotes.

Gram negative (−) organisms, such as *E. coli*, although synthesizing proteins containing signal peptides, do not usually secrete the proteins into the medium. Instead, such "secreted" proteins are exported to the periplasmic space between the inner and outer membranes of the Gram(−) bacterial cell wall. Even though *E. coli* has remained the prokaryotic organism of choice for cloning and other genetic manipulations, secretion of cloned gene products into the culture medium by *E. coli* from which the protein is generally readily isolatable has remained a formidable obstacle for commercializing biotechnology products. This is largely due to the fact that the outer membrane of Gram(−) bacteria is an effective barrier to release of proteins from the periplasmic space. In general, isolation of proteins produced by *E. coli* involves cell disruption followed by painstaking purification to separate the desired proteins from unwanted cellular products.

Gram positive (+) bacteria, such as *Bacillus* species, which have a single membrane and normally secrete a variety of proteins, are better organisms in which to produce large quantities of foreign proteins. On the one hand, a major advantage of Gram(+) production systems is that expressed gene products are secreted directly into the medium from which recovery and purification of the proteins are relatively easy. On the other hand, *Bacillus* species, particularly *B. subtilis*, have a drawback in they also secrete large amounts of proteolytic enzymes which can degrade a secreted protein, thereby resulting in significantly reduced yields of the protein. This particular disadvantage associated with the use of *Bacillus*, however, has been largely overcome by the recent development of substantially protease-free *Bacillus* organisms. See e.g., Kawamura, F. and R. H. Doi, J. Bacteriol. 160, 442–444 (1984).

Transformed Gram(+) organisms containing a vector carrying DNA encoding a foreign protein are, in principle, excellent hosts for high yield production of that protein. In order to be useful and practical the vectors should not only contain the structural gene sequence encoding the protein of interest, but also a DNA sequence encoding the promoter, ribosome-binding site and amino terminal signal sequence of a protein normally secreted by the host bacteria. For example see, e.g. U.S. Pat. No. 4,711,843 to Chang. The aforementioned promotor, ribosome-binding site and signal sequence allows the foreign protein to be produced and secreted by the host organism. There are, however, several problems associated with the use of such methods to produce large amounts of a specific protein.

The protein that is synthesized by the host is a fusion protein composed of the amino acid sequence of the predetermined protein of interest attached to the signal peptide of a host protein to allow for secretion of the product. In order for the desired protein to be readily separated from the part of the fusion protein needed for secretion, it is necessary to introduce specific cleavage sites into such fusion proteins. This has proven difficult to achieve. Also, as reported by Wickner and Lodish, Science 230: 400–407 (1985), a number of studies have shown that, although the signal sequence is clearly essential for secretion, it may not be sufficient by itself to promote secretion of a protein. The match between the signal sequence and mature secreted protein may be the critical limitation. Alternatively, other parts of the secreted protein may provide information specifying secretion.

It is also desirable, but not necessary, that the protein being secreted be tagged in some convenient way to make it readily detectable once produced. Furthermore, tagging of proteins also allows for identification of an organism producing the protein. The known tags currently used for such purposes are the enzymes β-galactosidase and alkaline phosphatase (see, for example, Matteucci et al., Biotechnology 4: 51-55 (1986). Although both enzymes are excellent tags and are easily detected by use of chromogenic substrates, they both have significant disadvantages rendering their value for large scale production of proteins relatively low.

β-galactosidase cannot be used as a protein tag if secreted proteins are desired since numerous studies have shown that β-galactosidase becomes lodged in the plasma membrane thereby preventing secretion of the tagged protein. Alkaline phosphatase, although exported to the periplasmic space of Gram(−) bacteria, cannot be used in Gram(+) secretion systems because it is readily degraded by extracellular proteases.

Staphylococcal nuclease has a number of advantages which makes it useful as a tag for proteins synthesized and secreted by both Gram(+) and Gram(−) organisms: (a) Digestion of the cloned staphylococcal nuclease gene with Sau3A yields a restriction fragment coding for the mature enzyme without its signal sequence thereby preventing secretion of such a truncated nuclease; (b) The presence of staphylococcal nuclease as part of a secreted protein is detectable by a rapid and sensitive colony assay; (c) Staphylococcal nuclease is relatively resistant to degradation by *Bacillis* proteases; (d) *B. subtilis* produces prenuclease which it secretes and correctly processes to mature nuclease; and (e) The N-terminus of mature staphylococcal nuclease is exposed to solvent and far removed from the active site, implying that fusion of foreign protein sequences to the N-terminus of nuclease would have little or no effect on the activity of the enzyme.

Lysostaphin is a bacteriocin which lyses staphylococci. Plasmid pRG5 containing a 1.5 Kb cloned DNA fragment which codes for preprolysostaphin has been described in U.S. patent application Ser. Nos. 852,407 and 034,464 filed in the name of Paul Recsei on Apr. 16, 1986, and Apr. 10, 1987, respectively, which are incorporated herein by reference, and in Reesi, Proc. Natl. Acad. Sci. 84: 1127-1131 (1987). Among other things, the 1.5 Kb gene encodes a 389 amino acid preprolysostaphin containing an amino terminal signal peptide of 36 amino acids. Adjacent to the C-terminal side of the signal peptide are seven tandem repeat prolysostaphin sequences, each containing 13 amino acids, which are removed during post-translational processing of preprolysostaphin to mature enzyme. Mature lysostaphin contains 246 amino acids and has an N-terminal sequence, Ala-Ala-Thr-His-Glu, which begins with amino acids 144-148 of the preprolysostaphin sequence.

Preprolysostaphin sequences have been cloned and expressed in E. coli, B. subtilis, and B. sphaericus 00. All three organisms efficiently and correctly process preprolysostaphin and secrete mature lysostaphin into the culture medium, indicating that the DNA sequence of the preprolysostaphin gene which codes for preprolysostaphin is useful for the construction of a Gram(+) [and Gram(−)] protein production system. Furthermore, predetermined proteins secreted by this production system can be tagged by staphylococcal nuclease, thus making the product and the organisms secreting it readily detectable.

SUMMARY OF THE INVENTION

A high-yield protein production system for use in Gram(+) organisms, and also Gram(−) organisms, has now been developed. The protein production system provides for recombinant autonomously replicable expression vectors containing portions of preprolysostaphin gene sequences which code for preprolysostaphin amino acid sequences necessary and sufficient to allow protein secretion (secretion sequence) and optionally staphylococcal nuclease gene sequences which code for a secretable and detectable nuclease enzyme protein tag (tag sequence). The preprolysostaphin DNA used in the production system encodes the signal peptide found in preprolysostaphin and varying amounts of the cleavable prolysostaphin tandem amino acid repeat sequences from none to the entire tandem repeat sequence of prolysostaphin, since efficiency of secretion and accuracy of processing may be dependent upon the amount of the proenzyme sequence present in the fusion.

In order to create the novel production system, a gene encoding a predetermined protein of interest (predetermined protein) is in one preferred embodiment inserted into a novel plasmid vector adjacent to and oriented on the 3' side of the DNA sequences which code for the preprolysostaphin protein secretion sequence such that the order of genes is 5'-vector DNA-secretion sequence-predetermined protein (−) sequence-vector DNA-3'. Transformation of host bacteria results in the synthesis of a hybrid fusion protein having an N-terminal preprolysostaphin sequence linked to the C-terminal predetermined protein of interest. After synthesis of the hybrid fusion protein, normal processing of the synthesized protein by the transformed host results in removal of the secretion sequence with accumulation of the predetermined protein.

In another preferred embodiment, the gene coding for the predetermined protein is inserted into the vector between DNA sequences coding for the preprolysostaphin protein secretion sequence and DNA sequences coding for the nuclease tag sequence such that the order of the genes in the system is 5'-vector DNA-secretion sequence-predetermined protein sequence-tag sequence-vector DNA-3'. Transformation of host bacteria with expression vectors containing this second-described genetic construct results in the synthesis of a tripartite fusion protein having an N-terminal preprolysostaphin-derived secretion sequence, a C-terminal nuclease tag, and a central amino acid sequence which is the predetermined protein of interest. After synthesis of the tripartite fusion protein, the secretion sequence is cleaved from the tripartite fusion protein by the normal processing mechanisms during and after secretion of the fusion protein by the transferred host bacteria. The protein which accumulates in the medium upon processing is essentially a two-part fusion protein having the cloned predetermined protein as its amino terminal portion and the nuclease tag sequence as its carboxy terminal portion. Transformed microorganisms secreting the predetermined protein can be readily detected by a colony assay using a chromogenic substrate specific for the staphylococcal nuclease tag.

The method of producing the tripartite fusion protein of the present invention also allows for easy and specific removal of the DNA sequences coding for the nuclease tag sequence from the expression vector once organisms producing and secreting the desired predetermined protein have been identified. After identification and isolation of transformed host microorganisms producing the predetermined protein, the DNA sequences coding for nuclease (tag sequence) are removable by specific endonuclease cleavage from the expression vector isolated from clones producing the predetermined protein. The resulting vector, now containing only the DNA sequences encoding the preprolysostaphin secretion sequence and the gene coding for the predetermined protein, is then reinserted into host organisms to obtain transformants expressing hybrid proteins having an N-terminal preprolysostaphin secretion sequence linked to a C-terminal predetermined protein. As a result of the normal processing of the preprolysostaphin secretion sequence by the host organism, the final product present in the culture medium is the mature, processed predetermined protein, essentially free of the preprolysostaphin secretion sequence.

The invention also provides for expression vectors suitable for producing hybrid and tripartite fusion proteins in both Gram(+) and Gram(−) organisms. Predetermined proteins which can be produced and secreted by the protein production system of the invention include, but are not limited to, viral proteins, bacterial proteins, hormones, enzymes, toxins, immunologic mediators, antigens, and pharmacologic mediators. Particularly preferred proteins include Interleukin-1 and human tissue plasminogen activator.

DESCRIPTION OF THE INVENTION

The present invention provides for recombinant autonomously replicatable expression vectors and a method for producing predetermined proteins which are secreted efficiently and in high yield from transformed host bacteria. In particular, the protein production system is especially useful for production and secretion of substantial quantities of predetermined proteins in Gram(+) organisms, especially *Bacillus*. The production system is also useful for producing proteins of interest in Gram (−) organisms.

The protein production system provides recombinant vectors containing DNA sequences coding for a fusion protein composed of N-terminal preprolysostaphin secretion sequences linked to a gene coding for the predetermined protein, which in turn may be optionally linked to DNA sequences coding for C-terminal nuclease tag sequences. The production system uses DNA fragments coding for preprolysostaphin obtained by Bal31 digestion of the plasmid pRG5 (which contains the entire 1.5 Kb preprolystostaphin gene). Such DNA fragments encode for at least the signal peptide (also called the presequence) and varying amounts of the proenzyme sequence (prolysostaphin) ranging from none to the entire prolysostaphin sequence. Prolysostaphin contains seven amino acid tandem repeats, each of which contains processing sites which allows for removal of the tandem repeats from the protein during processing of the preprolysostaphin to mature lysostaphin. Inclusion of the prolysostaphin tandem repeat sequences in the protein fusions of the invention provides compatibility between the preprolysostaphin signal sequence and the adjacent amino acid sequences of the predetermined protein and allows for efficient secretion of the predetermined protein. The tandem repeat sequences also provide convenient processing sites for removal of the preprolystostaphin sequences from the secreted protein product. Preprolysostaphin itself is properly secreted and processed by both Gram(+) (*Bacillus* spp.) and Gram(−) (*E. coli*) organisms as disclosed in U.S. patent application Ser. Nos. 852,407 and 034,464 in the name Recsei.

In a further embodiment, the protein production system may further preferably contain a truncated staphylococcal nuclease gene (tag sequence) which codes for the protein tag used to identify organisms secreting the predetermined protein. Sau3A digestion of the nuclease gene produces a 518 bp restriction fragment composed of an open reading frame followed by a translation stop codon and a transcription terminator. This nuclease gene fragment codes for a truncated form of nuclease enzyme without its signal peptide. The use of the nuclease DNA sequences which code for a tag sequence provides a means for identifying transformant hosts which are producing the protein of interest and for monitoring fusion proteins. The DNA sequences coding for nuclease, however, are not necessary for the expression or secretion of the predetermined protein by the transformed host.

Expression vectors have been constructed which contain only preprolysostaphin secretion sequences fused to the gene coding for the predetermined protein of interest. In this embodiment, which established the feasibility of this system, the truncated nuclease was defined as the predetermined protein. Transformation of bacteria by such vectors resulted in the expression of preprolysostaphin-nuclease fusion proteins which were readily processed by the host to mature staphylococcal nuclease. Transformed bacteria, preferably *E. coli. B. subtilis* and *B. sphaericus* 00, secreting properly processed nuclease were readily detected by a simple, rapid colony assay using a chromogenic substrate for nuclease. The assay involved growing bacterial colonies on agar plates which were then overlaid with agar containing DNA and toluidine blue. A colony with nuclease activity changes the color of the agar around the colony from blue to pink.

Furthermore, a protein production system which yields specific tagged tripartite fusion protein products can be constructed by inserting other genes which code for other specific predetermined proteins of interest (not nuclease) into the cloning vectors of the invention between the DNA sequences coding for preprolysostaphin and nuclease. The sequence of the DNA in the cloning vector thus is 5′-vector DNA-preprolysostaphin sequence-predetermined protein sequence-tag sequence-vector DNA-3′. Predetermined proteins which can be produced and secreted by the protein production system of the invention include, but are not limited to, viral proteins, bacterial proteins, hormones, enzymes, toxins, immunologic mediators, antigens, and pharmacologic mediators.

Human tissue plasminogen activator (TPA) and Interleukin-1 (Il-1) have been produced and secreted as tagged fusion proteins using the protein production system herein described. The protein products are composed of the particular predetermined protein sequence sandwiched between an N-terminal preprolysostaphin sequence and a C-terminal nuclease sequence, and have nuclease activity detectable by the nuclease colony assay. The preprolysostaphin portion of the fusion provides (a) an N-terminal signal sequence recognized by the secretion systems of *E. coli* and various Gram(+) organisms, especially *Bacillus* spp., and (b) proenzyme sequences compatible with tee signal peptide which contain multiple processing sites.

The invention also provides for the removal of the tag sequence once transformant host organisms producing the protein of interest have been identified. Preferably, the nuclease gene in the plasmids containing the DNA coding for the predetermined protein of interest is removed by specific endonuclease cleavage.

The invention further provides for expression vector libraries into which varying lengths of the preprolysostaphin gene (from about 350 to 900 bp) encoding the preprolysostaphin promoter, ribosome binding site, initiation codon, signal peptide and varying amounts of the prolysostaphin portion of preprolysostaphin (from 0 to 185 amino acids in length) and, optionally, the 518 bp Sau3A restriction DNA fragment from the nuclease gene have been inserted. The vectors contain specific restriction sites which allow insertion of a particular gene which codes for predetermined protein into the vectors at the 3' side of and adjacent to the DNA sequences coding for preprolysostaphin or between the DNA sequences coding for preprolysostaphin and nuclease. Furthermore, the vectors also permit easy removal of the nuclease gene sequences in order to produce non-tagged protein products. Expression vectors have been made which can be used to produce and secrete the predetermined proteins in both *E. coli* and in *Bacillus* species.

The following examples are provided to illustrate the invention and are not intended to limit the same.

EXAMPLE 1

Construction, and Expression of a Preprolysostaphin—Nuclease Fusion Library in *E. coli*

Figure 1:
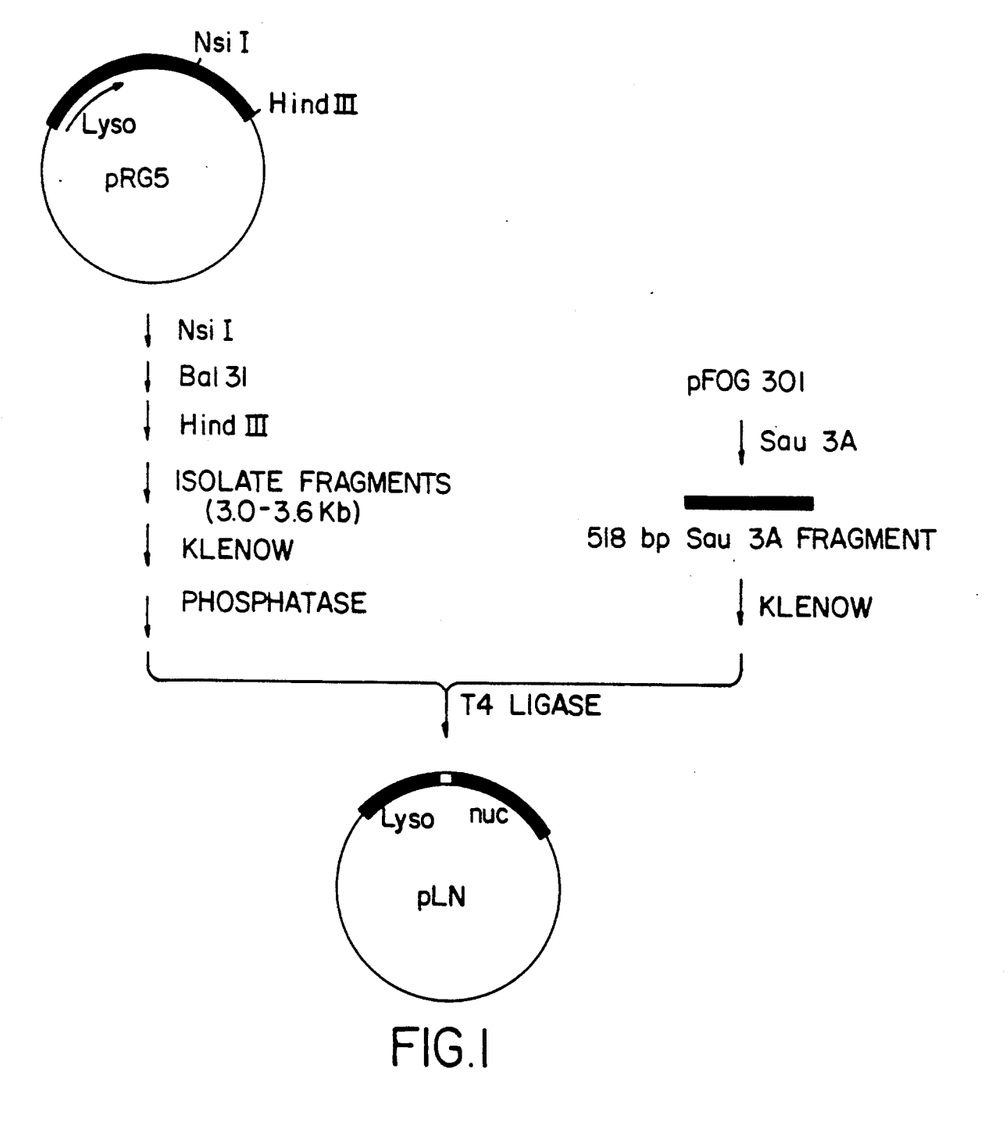
FIG. 1. Representation of the steps used to construct the lysostaphin-nuclease fusion library in E. coli JM105 using pUC8.

A library of preprolysostaphin-nuclease fusions was derived using plasmid pRG5 which carries the complete 1.5 Kbp preprolysostaphin gene. FIG. 1 is a diagrammatic representation of the steps used to construct the preprolysostaphin-nuclease library in *E coli* JM105. Construction of plasmid pRG5 and expression of lysostaphin were previously disclosed in U.S. patent application Ser. Nos. 852,407 filed Apr. 16, 1986 and 034,464 filed Apr. 10, 1987. The entire 1.5 Kbp preprolysostaphin gene sequence, including the presumed promoter site and preprolysostaphin encoded by the gene, are provided in Formula I of U.S. patent application Ser. Nos. 852,407 and 034,464 which is duplicated below. Any reference herein to sequence positions in the preprolysostaphin gene or in preprolysostaphin encoded thereby refers to such positions provided in Formula I.

FORMULA I

```
  1: ccggaactcttgaatgtttagttttgaaaattccaaaaaaaaacctactttcttaatatt

61: gattcatattattttaacacaatcagttagaatttcaaaaatcttaaagtcaatttttga

121: gtgtgtttgtatatttcatcaaaatcaatcaatattattttactttcttcatcgttaaaa

181: atggtaatatttataaaaatatgctattctcataaatgtaataataaattaggaggtatt

241: aaggttgaagaaaacaaaaaacaattattatacgagacctttagctattggactgagtac
     f-MetLysLysThrLysAsnAsnTyrTyrThrArgProLeuAlaIleGlyLeuSerThr 301: atttgccttagcatctattgtttatggaggattcaaaatgaaacacatgcttctgaaaa
     PheAlaLeuAlaSerIleValTyrGlyGlyIleGlnAsnGluThrHisAlaSerGluLys 361: aagtaatatggatgtttcaaaaaaagtagctgaagtagagacttcaaaagccccagtaga
     SerAsnMetAspValSerLysLysValAlaGluValGluThrSerLysAlaProValGlu 421: aaatacagctgaagtagagacttcaaaagctccagtagaaaatacagctgaagtagagac
     AsnThrAlaGluValGluThrSerLysAlaProValGluAsnThrAlaGluValGluThr 481: ttcaaaagctccagtagaaaatacagctgaagtagagacttcaaaagctccagtagaaaa
     SerLysAlaProValGluAsnThrAlaGluValGluThrSerLysAlaProValGluAsn 541: tacagctgaagtagagacttcaaaagctccggtagaaaatacagctgaagtagagacttc
     ThrAlaGluValGluThrSerLysAlaProValGluAsnThrAlaGluValGluThrSer 601: aaaagccccagtagaaaatacagctgaagtagagacttcaaaagccctggttcaaaatag
     LysAlaProValGluAsnThrAlaGluValGluThrSerLysAlaLeuValGlnAsnArg 661: aacagctttaagagctgcaacacatgaacattcagcacaatggttgaataattacaaaaa
     ThrAlaLeuArgAlaAlaThrHisGluHisSerAlaGlnTrpLeuAsnAsnTyrLysLys 721: aggatatggttacggtccttatccattaggtataaatggcggtatgcactacggagttga
     GlyTyrGlyTyrGlyProTyrProLeuGlyIleAsnGlyGlyMetHisTyrGlyValAsp 781: tttttttatgaatattggaacaccagtaaaagctatttcaagcggaaaaatagttgaagc
     PhePheMetAsnIleGlyThrProValLysAlaIleSerSerGlyLysIleValGluAla 841: tggttggagtaattacggaggaggtaatcaaataggtcttattgaaaatgatggagtgca
     GlyTrpSerAsnTyrGlyGlyGlyAsnGlnIleGlyLeuIleGluAsnAspGlyValHis 901: tagacaatggtatatgcatctaagtaaatataatgttaaagtaggagattatgtcaaagc
     ArgGlnTrpTyrMetHisLeuSerLysTyrAsnValLysValGlyAspTyrValLysAla 961: tggtcaaataatcggttggtctggagcactggttattctacagcaccacatttacactt
     GlyGlnIleIleGlyTrpSerGlySerThrGlyTyrSerThrAlaProHisLeuHisPhe 1021: ccaaagaatggttaattcattttcaaattcaactgcccaagatccaatgcctttcttaaa
      GlnArgMetValAsnSerPheSerAsnSerThrAlaGlnAspProMetProPheLeuLys 1081: gagcgcaggatatggaaaagcaggtggtacagtaactccaacgccgaatacaggttggaa
      SerAlaGlyTyrGlyLysAlaGlyGlyThrValThrProThrProAsnThrGlyTrpLys
```

FORMULA I -continued

1141: aacaaacaaatatggcacactatataaatcagagtcagctagcttcacacctaatacaga
ThrAsnLysTyrGlyThrLeuTyrLysSerGluSerAlaSerPheThrProAsnThrAsp 1201: taaaataacaagaacgactggtccatttagaagcatgccgcagtcaggagtcttaaaagc
IleIleThrArgThrThrGlyProPheArgSerMetProGlnSerGlyValLeuLysAla 1261: aggtcaaacaattcattatgatgaagtgatgaaacaagacggtcatgtttgggtaggtta
GlyGlnThrIleHisTyrAspGluValMetLysGlnAspGlyHisValTrpValGlyTyr 1321: tacaggtaacagtggccaacgtatttacttgcctgtaagaacatggaataaatctactaa
ThrGlyAsnSerGlyGlnArgIleTyrLeuProValArgThrTrpAsnLysSerThrAsn 1381: tactttaggtgttctttggggaactataaagtgagcgcgcttttataaacttatatgat
ThrLeuGlyValLeuTrpGlyThrIleLys 1441: aattagagcaaataaaaatttttctcattcctaaagttgaagc Plasmid pRG5 was cleaved at its unique NsiI site located within the preprolysostaphin gene at base pairs 914-919. The cleavage site is within the region of the preprolysostaphin gene coding for mature processed lysostaphin protein. Following NsiI cleavage, pRG5 was partially digested with Bal31 exonuclease to delete varying amounts of the preprolysostaphin gene. Fragments containing preprolysostaphin gene deletions ranging in size from a few base pairs to approximately 1 Kbp were purified by agarose gel electrophoresis and blunt-ended. The truncated nuclease gene fragment was prepared by digestion of the plasmic pFOG301 which contains the gene for staphylococcal nuclease with Sau3A and the 518 bp fragment derived from the nuclease gene was purified by preparative agarose gel electrophoresis. The fragment was blunt-ended and ligated to the DNA fragments derived from pRG5. The ligated DNA was then used to transform E. coli strain JM105. Transformants were grown on LB agar containing ampicillin (100 μm/ml) and overlaid with toluidine blue—DNA agar (Shortle, D., Gene, vol. 22, pp. 181-189 (1983)) to screen for nuclease activity.

Approximately 5% of JM105 transformants showed nuclease activity when assayed as described above. Plasmids isolated from nuclease producers contained the truncated nuclease gene fused to the preprolysostaphin gene at a variety of positions extending upstream from the vicinity of the NsiI site in the preprolysostaphin gene. (FIG. 1) The fusions coded for hybrid proteins having N-terminal preprolysostaphin sequences that varied in length from about 30 to 220 amino acid residues.

EXAMPLE 2

Expression and Secretion of Preprolysostaphin—Nuclease Fusions in *Bacillus*

The plasmid libraries coding for preprolysostaphin-nuclease fusions of Example 1 were transferred from E. coli to B. subtilis strain BD170 as pBC16 cointegrates. Plasmid pBC16, obtained from the collection of Richard P. Novick, Public Health Research Institute, New York, N.Y., was isolated from soil bacilli and is highly homologous to and incompatible with pUB110, a S. aureus plasmid specifying kanamycin resistance.

pBC16 DNA was isolated from B. subtilis by the alkaline-SDS procedure described by Birnboim, Meth. Enzymol, Vol. 100, pp. 243-255 (1983). Cells from a 250 ml overnight culture grown in VY medium (25 g Difco veal infusion; 5 g Difco yeast extract per liter H₂O) were harvested by centrifugation, washed in TE buffer and resuspended in 5 ml of TEG buffer (25 mM Tris, 10 mM EDTA, 50 mM glucose, pH 8.0). Lysozyme (1 mg/ml) was added and the suspension was incubated at room temperature for 20 minutes. After addition of 10 ml of 0.2% NaOH-1% SDS, the mixture was incubated at 0° C. for 45 minutes. Ten ml of 3M potassium acetate—1.8M formic acid were then added and the mixture was further incubated at 0° C. for 30 minutes. The lysate thus obtained was centrifuged at 15,000×g for 20 minutes. Two volumes of 95% ethanol were added to the supernatant and the resulting precipitate, obtained after 15 minutes at room temperature, was collected by centrifugation at 10,000×g for 10 minutes, washed with 80% ethanol and dissolved in 0.5 ml TE buffer. Approximately 200 μg of closed circular pBC16 DNA was obtained with this procedure.

For cointegrate formation, pBC16 and the pUC8-based plasmids containing in frame preprolysostaphin-nuclease fusions were cleaved with EcoRI and ligated to one another, with the ligated DNA being used to transform E. coli JM105. Clones with cointegrates were selected by growing transformants on LB agar containing tetracycline (5 μg/ml). Cointegrate plasmid DNA was then isolated from a pool of one hundred tetracycline-resistant clones and used to transform frozen competent cells of B. subtilis BD170 obtained from the collection of Dr. David Dubnau, Public Health Research Institute, New York, N.Y. Cells were grown on GL agar containing tetracycline (15 μg/ml) and a number of clones which retained the nuclease-positive phenotype upon repeated streaking were isolated. When these clones were grown in CYGP liquid medium containing tetracylcine (25 μg/ml), all the cells retained the tetracycline-resistant, nuclease-positive phenotype. Based on measurements of nuclease activity, several clones consistently produced about 50 mg of fusion protein per liter of culture.

Figure 2:
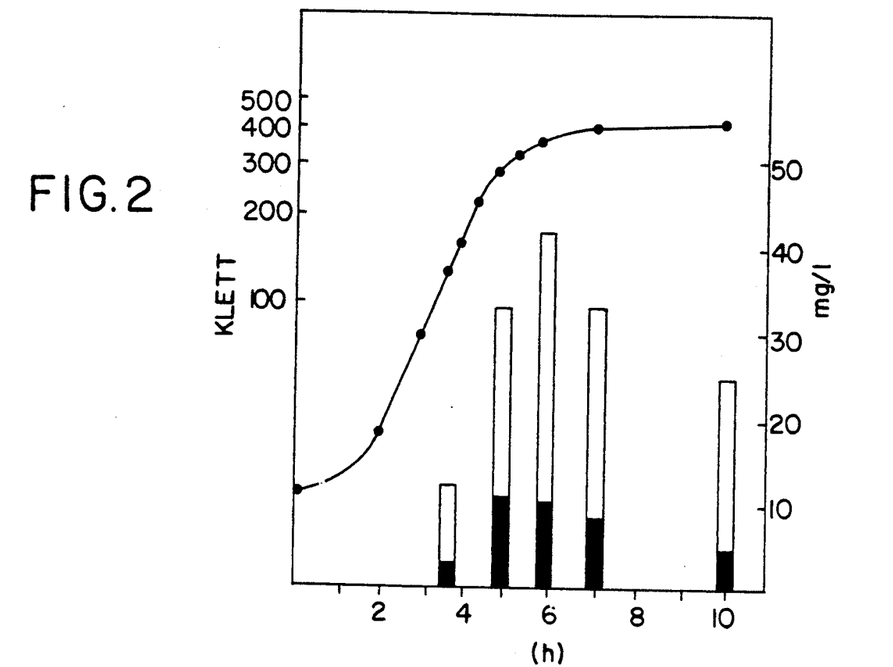
FIG. 2. Production and secretion of lysostaphinnuclease fusion proteins by cultures of *B. subtilis* BD170 clone T170.

For example, FIG. 2 depicts the production and secretion of a preprolysostaphin-nuclease fusion protein in cultures of one such clone, B. subtilis BD170 clone T170. Restriction analysis of the recombinant cointegrate plasmid in clone T170 had shown that it encodes a hybrid protein composed of the N-terminal preprolysostaphin sequence (110 amino acids) fused to a modified form of nuclease A (154 amino acids). To analyze production of nuclease, transformant cells were grown in CYGP medium containing tetracycline (25 ug/ml) at 37° C. in shaker flasks. Cell pellets were suspended in 0.05 M Tris, pH 8.8 and sonicated for two minutes. In FIG. 2 the amount of the nuclease protein product in culture supernatants (open bars) and cell extracts (solid bars) is based on nuclease activity. As shown in FIG. 2, at least 75% of the total nuclease activity in *B. subtilis* BD170 clone T170 cultures was present in the supernatant, indicating that the preprolysostaphin-nuclease hybrid proteins were efficiently secreted from the cell.

That the nuclease present in the supernatant of *B. subtilis* BD170 clone T170 cultures was accurately processed to mature active nuclease was indicated by Western blot analysis. A culture of clone T170 was grown as described above. Supernatant fractions and cell extracts were prepared when the culture reached Klett 300, 350 and 400, respectively. After electrophoresis, the proteins were blotted and the blot was reacted first with rabbit antibodies to nuclease followed by goat antibodies to rabbit IgG which had been conjugated to alkaline phosphatase. The blot was then stained as described by Blake et al., *Anal. Biochem,* vol. 136, pp. 175-179, 1984. The Western blot analysis demonstrated that, although some higher molecular weight hybrid forms were present in cellular and supernatant fractions, most of the cross-reacting nuclease in the supernatant of *B. subtilis* clone T170 was indistinguishable from mature nuclease produced by staphylococci.

In this case a hybrid fusion protein containing a preprolysostaphin sequence was correctly and efficiently processed by *B. subtilis* to generate the desired protein product. This Example demonstrates that hybrid fusion proteins which are correctly processed by the host to the mature predetermined protein of interest can be produced by this system. In this Example, nuclease is actually the predetermined protein of interest (not the tag). The following Examples demonstrate the production of tripartite fusions where nuclease is used as the tag for the predetermined protein of interest.

EXAMPLE 3

Construction of Tripartite Fusions

The complete tagged protein production system yields tripartite fusion proteins which are composed of the foreign protein of interest sandwiched between an N-terminal preprolysostaphin sequence and a C-terminal nuclease sequence. Since these fusion proteins have nuclease activity, transformant host bacteria producing the fusion proteins have nuclease activity and are readily detectable by the colony assay described above. The preprolysostaphin provides both an N-terminal signal sequence recognized by both *E. coli* and *Bacillus spp.* and proenzyme (i.e. prolysostaphin) sequences compatible with the signal peptide which contain multiple processing sites. Since efficiency of secretion and accuracy of processing vary on a case by case basis according to the amount of proenzyme sequence present in the tripartite fusion, vectors have been constructed which code for varying amounts of the preproenzyme sequences (from about 36 to 220 residues).

Figure 3:
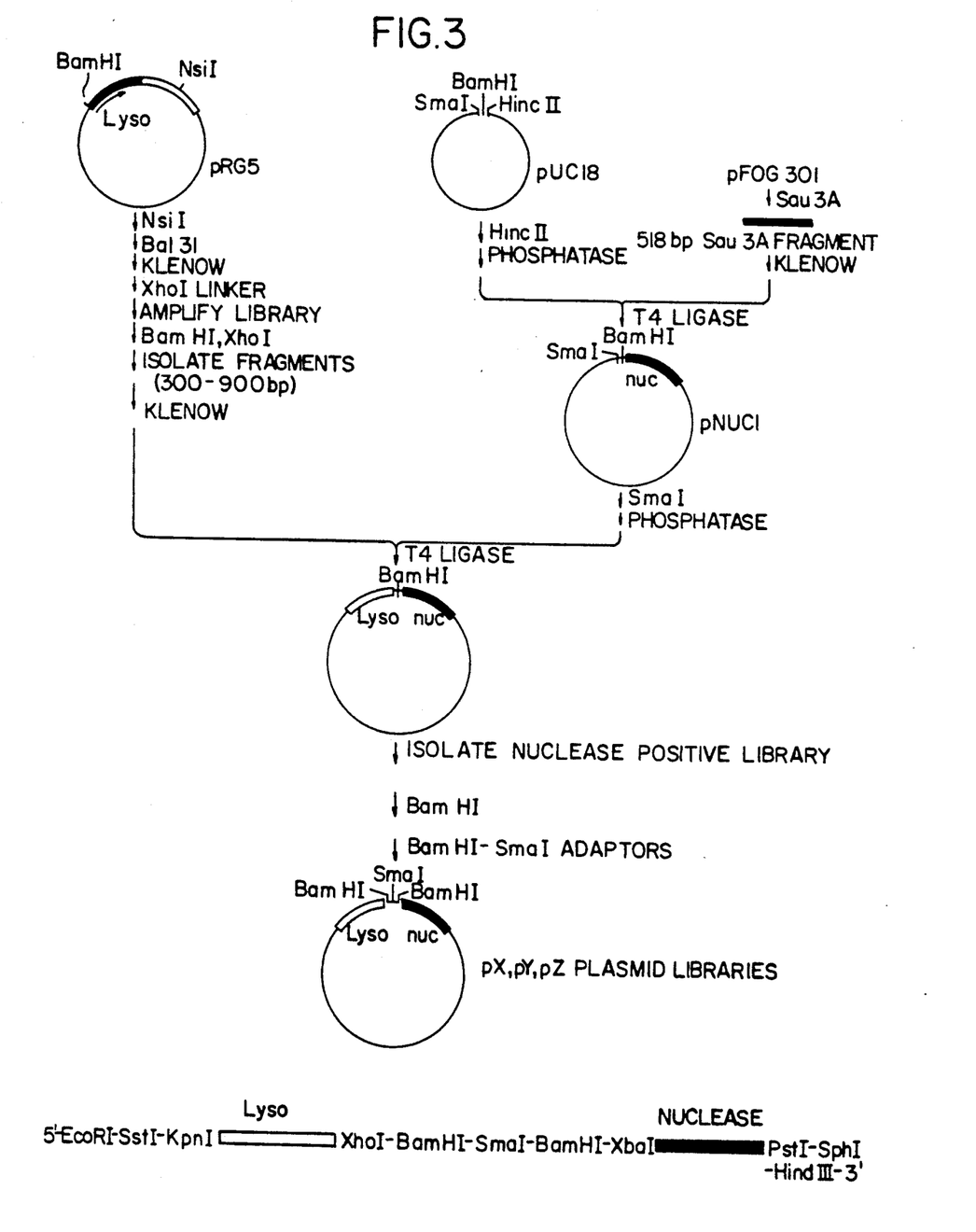
FIG. 3. Diagrammatic representation of the steps used to construct the tripartite fusion system based on the lysostaphin and nuclease genes.

With reference to FIG. 3, the following steps were used to construct the tripartite fusion system based on the preprolysostaphin and nuclease genes. For convenience, the system was first assembled in *E. coli* JM105 using pUC18 as the vector and then transferred to *Bacillus* expression vectors for use in *Bacillus* spp. The restriction sites present in the cloning system are shown at the bottom of FIG. 3.

(a) Sau3A digestion of pFOG 302, a recombinant plasmid described by Shortle, D., Gene, vol. 22, pp. 181-189 (1983) containing the nuclease gene, yields a unique 518 bp fragment which begins within the coding region between nuclease B and A and extends beyond the termination codon and transcription termination site of the gene. This fragment codes for a modified nuclease composed of nuclease A plus an N-terminal extension of six amino acids. The initial step in the construction of the tripartite expression system was the cloning of the blunt-ended Sau3A nuclease fragment into the HincII site of pUC18. Recombinant plasmids were selected on the basis of their β-galactosidase-negative phenotype (resulting from insertional inactivation of the lacZ' gene of pUC18) and clones with the nuclease insert in the same orientation as the lacZ' gene were identified by restriction analysis with HindIII. The desired clone had a HindIII site at basepairs 319-324 of the nuclease insert and a second HindIII site immediately downstream from the insert. In this construct, the nuclease insert was out of frame with respect to lacZ' and the desired clone had a nuclease-negative phenotype. This clone was referred to as pNUC1.

(b) The second step of the construction was to create preprolysostaphin-nuclease hybrids by fusing DNA fragments of the preprolysostaphin gene to the nuclease gene. The preprolysostaphin gene fragments, which contain elements required for initiation of transcription and translation as well as varying amounts of the structural gene, were prepared as follows: pRG5, the recombinant plasmid derived from pUC8 which contains the preprolysostaphin gene, was digested with NsiI to cut the plasmid at its unique NsiI site located at base pairs 914-919 of the preprolysostaphin gene. The plasmid was partially digested with Bal31 exonuclease to remove varying amounts of the lysostaphin sequence. The DNA was then blunt-ended, ligated to XhoI linkers, digested with XhoI and religated. *E. coli* JM105 was transformed with the ligated DNA to create a library of DNA fragments coding for preprolysostaphin. These fragments were then excised by digestion of the pooled DNA with BamHI and XhoI, purified by preparative gel electrophoresis, blunt-ended and cloned into the SmaI site of pNUC1 (FIG. 3). In frame preprolysostaphin-nuclease fusions were selected on the basis of their nuclease-positive phenotypes and the sizes of the preprolysostaphin gene fragments present in the fusions were determined by digestion with KpnI and XhoI. (The XhoI cleavage site had been recreated at the 3' end of the preprolysostaphin gene fragment when it was inserted in the proper orientation into the SmaI site of pNUC1.)

(c) Fifty nuclease-positive clones with DNA fragments coding for preprolysostaphin and ranging in size from about 350 to 900 bp were pooled and digested at the unique BamHI site situated between the preprolysostaphin and nuclease DNA sequences (FIG. 3). Three different nonphosphorylated BamHI-SmaI adaptors (10, 12 and 14 nucleotides in length) were ligated to the BamHI digested DNA to create three sets of vectors. Two of these sets contain either one or two extra base pairs on either side of the SmaI cloning site and were called pY and pX, respectively. They were selected on the basis of their nuclease-negative (nuc⁻) phenotype. The third set, called pZ, is in-frame and is nuclease-positive (nuc⁺). Each of the three sets was composed of fifty (50) different clones. The presence of the SmaI cloning site in each clone was verified by restriction analysis.

Figure 4:
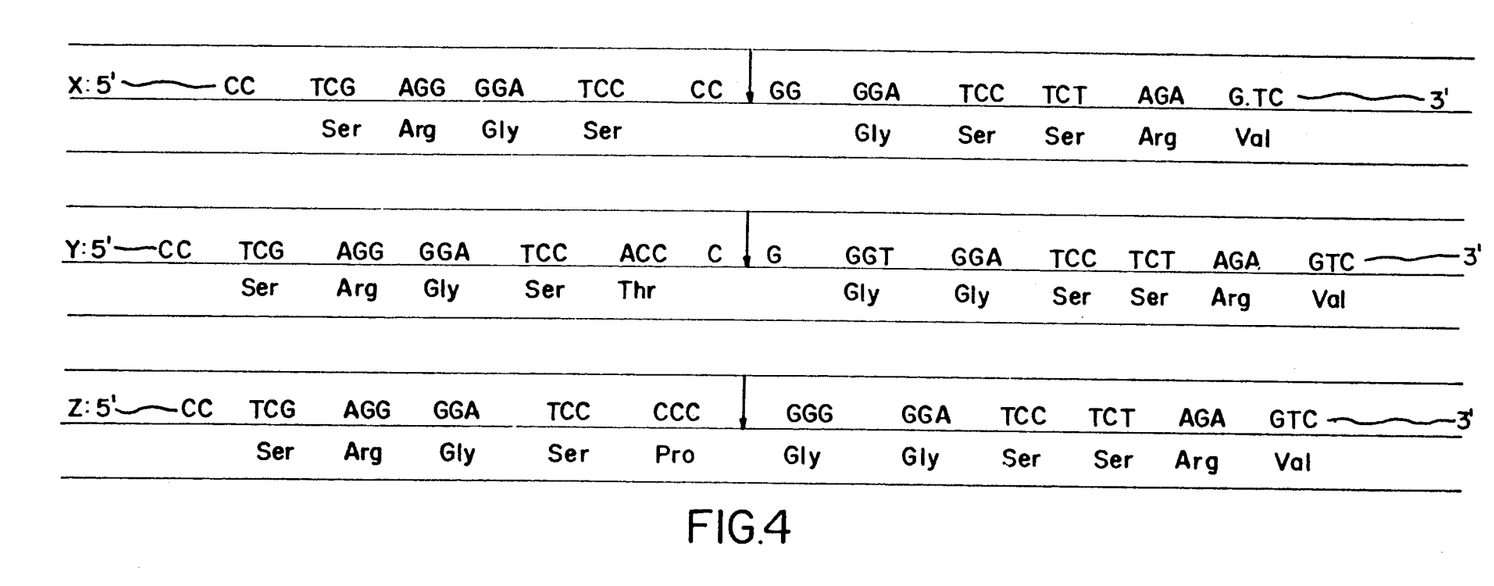
FIG. 4. Cloning sites of the tripartite fusion vectors, pX, pY, and pZ.

FIG. 4 depicts the cloning sites of the tripartite fusion vector sets pX, pY and pZ, according to the invention. "Plasmids containing plasmide pX, pY and pZ have been deposited in the American Type Culture Collection, 12301 Parklawn Drive, Rockville, Md. 20852 and assigned accession numbers ATCC 68221, 68222, and 68223 respectively. The encoded amino acid sequence is given below the DNA sequence for each set of vectors. Each DNA sequence contains XhoI-BamHI-SmaI-BamHI-XbaI restriction sites extending in a 5' to 3' orientation. The arrow indicates the SmaI cleavage site. DNA coding for the predetermined protein, which has been randomized by sonication, treatment with DNase I, digestion with Bal31 exonuclease, or other known methods is cloned into the SmaI sites of either one of the two nuc⁻ sets of vectors (pX, pY). Clones expressing foreign DNA are then detected on the basis of their nuc⁺ phenotype. A symmetrical open reading frame with a defined sequence is cloned into one set of vectors to yield an in-frame tripartite fusion. When the nuc⁺ set of vectors (pZ) is used for cloning, the SmaI digested vectors are treated with alkaline phosphatase to reduce the background of nuc⁺ clones which do not have inserts. In the case of inserts which are known not to recreate or contain a SmaI site, the ligated DNA is digested with SmaI to recut self-ligated vector DNA.

EXAMPLE 4

Figure 5:
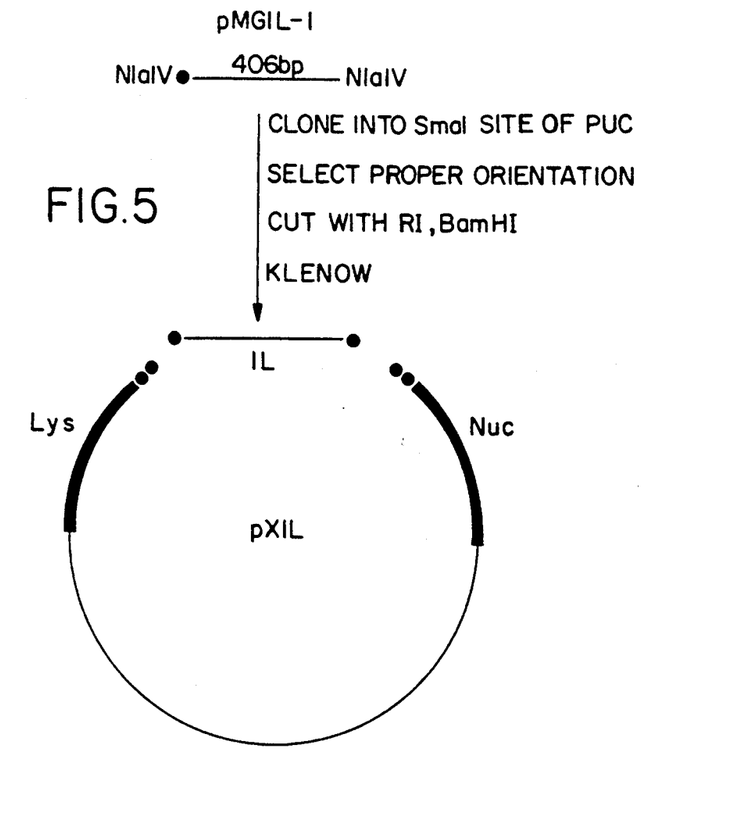
FIG. 5. Strategy used for converting the 406 bp NlaIV fragment derived from the IL-1 gene into a symmetrical open reading frame fragment with one extra base pair on either end.

Construction and Expression of an Interleukin-1 Tripartite Fusion (a) An IL-1 open reading frame DNA with symmetrical ends which could be inserted into the expression vectors was prepared as follows:

Plasmid pMGIL-1 (obtained from SmithKline Beckman) which contains the gene coding for interleukin-1 (IL-1) was digested with NlaIV. A 406 bp fragment derived from the IL-1 coding sequence was isolated. As depicted in FIG. 5, this fragment, which contains one extra base pair at its 5'-end and is in-frame at the 3'-end, was cloned into the SmaI site of pUC19. Plasmid DNA was isolated from clones that contained the fragment inserted in the opposite orientation with respect to lacZ'. The DNA was then digested with EcoRI and BamHI and blunt-ended with the Klenow fragment of DNA polymerase I to generate a 431 bp open reading frame with one extra base pair at either end. The procedure resulted in the addition of 18 bp to the 5' end and 7 bp to the 3' end of the fragment. The fragment was then gel purified and, as shown in FIG. 5, cloned into the SmaI site of the pX set of expression vectors.

(b) IL-1 containing plasmids with in frame fusions were isolated as follows:

The pX set of vectors was digested with SmaI, treated with alkaline phosphatase, ligated to the symmetrical 431 bp IL-1 fragment and the ligated DNA was used to transform *E. coli* JM105. About 2000 transformants were overlaid with toluidine blue-DNA agar to test for nuclease activity as described in Example 1. Approximately 5% of the transformants showed strong nuclease activity, 45% had moderate activity, and 50% had no nuclease activity. Restriction analysis using BamHI and HindIII showed that all of the transformants with moderate activity contained the IL-1 insert in the proper orientation. Transformants with strong nuclease activity had no insert and presumably arose as a result of frame shift mutations that occurred during the cloning. Transformants with no nuclease activity either contained no insert, or contained the insert in the wrong orientation.

Plasmids from nuclease-positive clones with apparent in-frame fusions were found to encode N-terminal preprolysostaphin sequences ranging in size from about 30 to 150 amino acids. Forty such plasmids were pooled and designated the pX-IL library. (FIG. 5).

(c) In-frame Interleukin-1 fusions in *B. subtilis* were expressed as follows:

The tripartite IL-1 fusions were then expressed in *B. subtilis*. For this purpose, substantially protease-deficient strains of *B. subtilis* were produced. The two major proteases of *B. subtilis* (subtilisin, a serine protease optimally active at alkaline pH and thermolysin, a metalloprotease optimally active at neutral pH) were eliminated from several strains of *B. subtilis*, including strain BD170 by replacing active protease genes with inactive ones.

Figure 6:
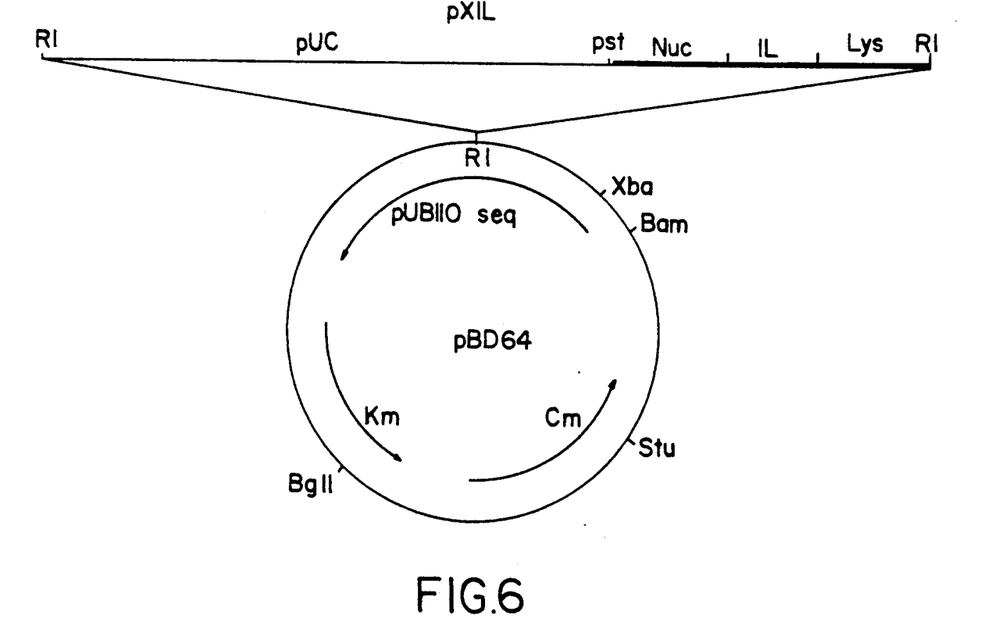
FIG. 6. Construction of the pXIL-pBD64 cointegrates.

The *Bacillus* plasmid pBD64, which transfers resistance to chloramphenicol and kanamycin, was used to construct cointegrates for transfer of the apparent in-frame fusions into *Bacillus*. The pX-IL library was first linearized with EcoRI, blunt-ended and then ligated to pBD64 that had been linearized and blunt-ended at its unique EcoRI, BamHI, or BglII site (FIG. 6). The ligated DNA was used to transform *E. coli* JM105 and clones containing cointegrates were selected on the bais of their chloramphenicol resistance (Cmʳ). The clones were all nuclease positive (Cmʳ nuc⁺).

Cointegrates from a pool of 50 such Cmʳ nuc⁺ clones were transferred into a double protease-minus *B. subtilis* BD170 host strain produced as described above. Cmʳ, nuc⁺ transformants were isolated and repeatedly streaked on plates containing chloramphenicol to test for stability. Five clones, designated 1.8, 1.10, 1.16, 2.3, and 2.4, showed stable phenotypes upon repeated passage on agar. When these clones were grown in chloramphenicol-containing liquid medium, all cells retained the Cmʳ nuc⁺ phenotype. The data in Table I show that several of these clones consistently produced at least 40 mg/l of the interleukin-1-nuclease fusion based on activity measurements, with about 80% of the nuclease activity present in the supernatant fraction of the cultures.

TABLE I

| PRODUCTION OF INTERLEUKIN-1-NUCLEASE FUSIONS | | | |
| --- | --- | --- | --- |
| | | Fusion Protein Produced (mg/liter) | |
| Clone | Culture OD (KU) | Supernatant | Cell Pellet |
| 1.8 | 300 | 5.6 | 0.7 |
| | 350 | 6.8 | 1.9 |
| | 400 | 11.2 | 2.3 |
| 1.10 | 300 | 20.1 | 2.4 |
| | 350 | 29.8 | 3.5 |
| | 400 | 43.7 | 7.5 |
| 1.16 | 300 | 23.6 | 5.6 |
| | 350 | 36.8 | 12.3 |
| | 400 | 45.5 | 9.1 |
| 2.3 | 300 | 5.4 | 0.4 |
| | 350 | 6.3 | 0.9 |
| | 400 | 5.6 | 0.7 |
| 2.4 | 300 | 19.3 | 8.8 |
| | 350 | 38.5 | 9.6 |
| | 400 | 43.9 | 9.8 |

Production of interleukin-nuclease fusions in *B. subtilis* BD170 DP−. Cells were grown in VY medium containing chloramphenicol (5 ug/ml) at 37° with vigorous aeration. PMSF (1 mM) was added at 200 Klett Units and again at the time of harvest. The quantities of protein produced are based on measurements of nuclease activity.

Clone 1.16, which showed the highest levels of activity, was selected for further analysis. Restriction analysis showed that the p1.16 cointegrate coded for a tripartite fusion protein containing an N-terminal preprolysastaphin sequence of about 80 amino acids and a molecular weight of about 39,000 daltons. Western blot analysis of cell extracts of clone 1.16 indicated the presence of the 39,000 dalton protein which was recognized by antibodies to both interleukin-1 and to nuclease. Clone 1.16 cultures had been grown in VY medium containing chloramphenicol (5 ug/ml) at 37° C. with vigorous aeration. Protease inhibitors were added when the cultures reached 220 Klett units and again at the time of harvest. Cells were harvested by centrifugation, washed with 10 mM Tris, pH 8.8, 30 mM in NaCl resuspended in this same buffer (the original culture volume) and sonicated for 2 min at 0° C. Samples were then subjected to SDS gel electrophoresis and Western blot analysis. Blots were first incubated with rabbit antibodies to nuclease or rabbit antibodies to interleukin-1 and then detected with a goat anti-rabbit IgG-alkaline phosphatase conjugate as described. Samples were taken at 300, 370 and 420 Klett units. Cultures were grown in the presence of (a) 1 mM PMSF or (b) 1 mM PMSF, antipain (1 mg/ml), leupeptin (1 mg/ml). The interleukin-1 standard was run as a control.

Western blot analysis showed that cell extracts of clone 1.16 contained essentially no lower molecular weight cross-reacting material, indicating that the tripartite fusion protein accumulated intracellularly with little or no degradation. As a control, clones containing a pUC18-pBD64 cointegrate contained no tripartite fusion protein product.

Western blot analysis of supernatant fractions from clone 1.16 showed the presence of a 37,000 dalton protein which reacts with anti-interluekin-1 and anti-nuclease antibodies was readily apparent. The removal of the preprolysostaphin signal peptide from the encoded 39,000 dalton tripartite fusion protein gene product would be expected to result in a protein having a molecular weight of about 37,000 daltons.

The culture supernatant fractions from clone 1.16 also contained lower molecular weight cross-reacting material which indicated that some degradation of the product occurred during or after secretion. Experiments were performed to determine whether such degradation was a result of residual protease activity in the culture. Growth conditions and procedures were identical to those described for the experiment described for the clone 1.16, with the exception that various protease inhibitors were added to the cultures to minimize degradation of the secreted product. Samples were taken at 300 (1) and at 370 (2) Klett units. The following inhibitors were added to the culture: PMSF, PMSF, and antipain, PMSF and leupeptin, PMSF, antipain, and leupeptin, antipain and leupeptin. The blots were reacted with antibodies to interleukin-1. The interleukin-1 standard was run as a control. The results showed that addition of the protease inhibitors phenylmethylsulfonyl fluoride (PMSF) and antipain to the culture medium significantly reduced degradation of the product, thus indicating that the degradation most likely resulted from residual protease activity in the culture.

EXAMPLE 5

Tissue Plasminogen Activator Fusions

Plasmid pDSP1.1 TPA 25 BGH, (obtained from Smith Kline/Beckman) which contains the gene for human tissue plasminogen activator (TPA) was digested with BglII and BstEII and blunt-ended. The 1,546 bp TPA gene fragment, which contains two extra baspairs at each end, was gel purified and cloned into the SmaI site of the pY set of expression vectors. E. coli JM105 was transformed with the ligated DNA. About 80% of the E. coli clones with low nuclease activity following transformation contained the TPA gene insert. In all cases the insert was present in the proper orientation. DNA from 10 clones with apparent inframe fusions was pooled and used to construct pBD64 cointegrates which were then used to transform B. subtilis. Eight transformant B. subtilis clones which remained nuc+ upon repeated restreaking were isolated. These clones, when grown in liquid medium, produced less than 30 µg/l nuclease, based on activity measurements. Western blots showed the presence of small amounts of nuclease, but no higher molecular weight cross-reactive material in supernatants and cell extracts from these cultures.

Figure 7:
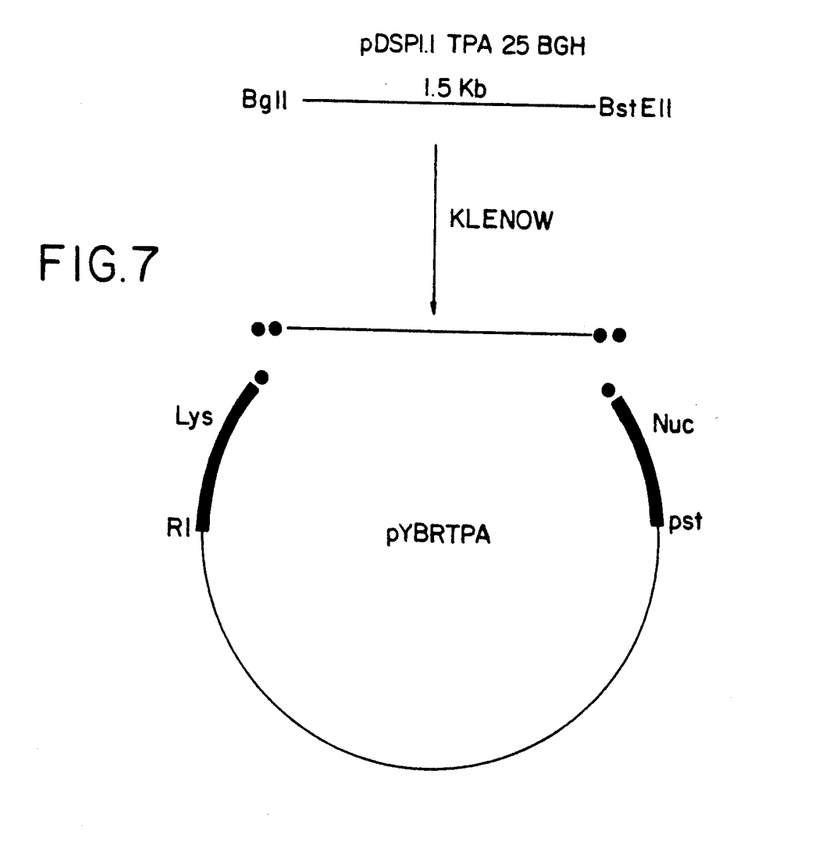
FIG. 7. Cloning the blunt-ended 1,546 bp BglII/BstEII fragment derived from the TPA gene into the SmaI site of the pYBR set of expression vectors.

In a second attempt, a pBR322-based expression system was produced by replacing the 752 bp EcoRI-PstI fragment of pBR322 (this nonessential fragment extends from bp 3609 to bp 4361 of the plasmid and contains part of the amp gene) with the 0.9 to 1.4 Kbp Eco RI-PstI fragments from pY which contain the preprolysostaphin-nuclease fusions. This set of vectors has been designated pYBR. The 1.5 Kbp TPA fragment was blunt-ended and then ligated to the pYBR vectors which had been cut with SmaI as shown in FIG. 7 and the ligated DNA was then used to transform E. coli strain DH5. Fourteen clones which were resistant to tetracycline and had low levels of nuclease activity were isolated and further characterized by restriction analysis with BamHI, PstI and EcoRI. Twelve of these clones contained the TPA insert in the proper orientation with respect to the preprolysostaphin-nuclease fusion.

Western blot analysis of nuclease-positive clones of E. coli DH5 transformants with TPA inserts showed that each of the clones produced protein which reacts with antibodies to both nuclease and TPA. Transformant DH5 cells were grown in LB medium containing tetracycline (10 mg/ml) at 37° C. with aeration to early stationary phase. Cells were harvested by centrifugation, suspended in 0.01 M Tris, pH 7.5 containing 2 mM PMSF and 1 mM pHMB (one tenth of the original culture volume) and sonicated for 2 min at 0° C. Blots were incubated with rabbit antiserum to nuclease or rabbit antiserum to TPA. The rabbit antiserum to nuclease blot was further incubated with goat antibodies to rabbit IgG conjugated to alkaline phosphatase and stained for alkaline phosphatase activity. The rabbit antiserum to TPA blot was further incubated with radioiodinated protein A and subjected to autoradiography. Samples 1 to 6 are nuclease-positive clones with TPA inserts in the proper orientation. Sample N is a clone which contained the cloning vector without an insert. The observed molecular weights of the cross-reactive proteins indicated that the TPA protein products generally accumulated inside the cells with little or no degradation, although partial degradation was observed in some cases. The TPA product was not present in the periplasm. These clones produced about 1 mg per liter of the recombinant TPA protein based on nuclease activity measurements.

I claim:

1. Recombinant cloning vector for expression and secretion of a predetermined protein in a transformant microbial host comprising an autonomously replicatable expression vector which can transform a microbial host and express and secrete a predetermined protein therein, the vector comprising a hybrid DNA sequence having at least two DNA sequences; a first sequence which codes for a preprolysostaphin amino acid sequence necessary and sufficient to allow protein secretion, and a second sequence which codes for the predetermined protein, wherein the second sequence is insertable into the vector so as to be located adjacent to and oriented on the 3' side of the first sequence.

2. Recombinant vector according to claim 1 wherein the protein secretion sequence comprises the signal peptide of preprolysostaphin.

3. Recombinant vector according to claim 1 wherein the protein secretion sequence comprises the signal peptide of preprolysostaphin together with at least one tandem amino acid repeat sequence of the prolysostaphin portion of preprolysostaphin.

4. Recombinant cloning vector according to claim 1 further comprising a third DNA sequence in the vector which codes for a secretable and detectable protein tag comprising staphylococcal nuclease, the third DNA sequence being located in the vector adjacent to and oriented on the 3' side of the insertable gene coding for the predetermined protein.

5. Recombinant cloning vector according to claim 4 wherein the third DNA sequence is staphylococcal nuclease from which the signal peptide has been removed.

6. Recombinant cloning vector according to claim 4 in which the cloning vector is selected from the group of vectors consisting of plasmid library pX, plasmid library pY, and plasmid library pZ.

7. Recombinant cloning vector according to claim 4 in which the cloning vector is at least one plasmid selected from the pX plasmid library.

8. Recombinant cloning vector according to claim 4 in which the cloning vector is at least one plasmid selected from the pY plasmid library.

9. Recombinant cloning vector according to claim 4 in which the cloning vector is at least one plasmid selected from the pZ plasmid library.

10. Recombinant cloning vector according to claim 1 wherein the predetermined protein is selected from the group of proteins consisting of viral proteins, bacterial proteins, hormones, enzymes, toxins, immunologic mediators, antigens, and pharmacologic mediators.

11. Recombinant cloning vector according to claim 1 wherein the predetermined protein is Interleukin-1.

12. Recombinant cloning vector according to claim 1 wherein the predetermined protein is tissue plasminogen activator.

13. Recombinant cloning vector according to claim 1 wherein the microbial host is selected from the group consisting of *B. subtilis* and *E. coli*.

14. Recombinant cloning vector according to claim 1 wherein the microbial host is *B. subtilis*.

15. Recombinant cloning vector according to claim 14 wherein the *B. subtilis* is double protease-minus.

16. Recombinant cloning vector according to claim 1 wherein the microbial host is *E. coli*.

17. Method for producing a predetermined protein comprising:
(a) inserting a DNA sequence coding for the predetermined protein into a recombinant cloning vector capable of autonomous replication in a microbial host and expression of proteins therein, the gene being inserted into the vector so as to be located adjacent to and oriented on the 3' side of a sequence in the vector coding preprolysostaphin amino acid sequence necessary and sufficient to allow protein secretion, thus constructing a hybrid DNA sequence the vector being capable of expressing the predetermined protein in a transformant microbial host.
(b) transforming a suitable microbial host with the recombinant vector to produce a transformant microbial host which expresses and secretes the predetermined protein;
(c) culturing the transformant microbial host in a suitable culture medium; and
(d) isolating the predetermined protein from the culture medium.

18. Method according to claim 17 wherein the protein secretion sequence is the signal peptide of preprolysostaphin.

19. Method according to claim 17 wherein the protein secretion sequence comprises the signal peptide of preprolysostaphin together with at least one tandem amino acid repeat sequence of the prolysostaphin portion of preprolysostaphin.

20. Method according to claim 17 wherein the recombinant vector contains additional DNA sequences which code for staphylococcal nuclease, the additional DNA sequences coding for a secretable and detactable protein tag comprising staphylococcal nuclease, the additional DNA sequences being located in the vector before inserting the gene for the predetermined protein adjacent to and oriented on the 3' side of the DNA sequences coding for preprolysostaphin.

21. Method according to claim 20 wherein the DNA sequence coding for the predetermined protein is inserted in the vector between the DNA sequences coding for preprolysostaphin and the additional DNA sequences coding for staphylococcal nuclease, such that the DNA sequence being inserted into the vector is located in the vector adjacent to and oriented on the 3' side of the DNA sequences coding for preprolysostaphin and adjacent to and oriented on the 5' side of the additional DNA sequences coding for staphylococcal nuclease.

22. Method according to claim 21 further comprising identifying the transformant microbial hosts expressing the predetermined protein and detecting expression and secretion of the predetermined protein by means of an assay for staphylococcal nuclease.

23. Method according to claim 20 wherein the protein tag sequence is staphylococcal nuclease from which the nuclease signal peptide has been removed.

24. Method according to claim 20 wherein the recombinant vector is selected from the group of vectors consisting of plasmid library pX, plasmid library pY, and plasmid library pX, plasmid library pY, and plasmid library pZ.

25. Method according to claim 20 wherein the vector is at least one plasmid selected from the pX plasmid library.

26. Method according to claim 20 wherein the vector is at least one plasmid selected from the pY plasmid library.

27. Method according to claim 20 wherein the vector is at least one plasmid selected from the pZ plasmid library.

28. Method according to claim 17 wherein the predetermined protein is selected from the group of proteins consisting of viral proteins, bacterial proteins, hormones, enzymes, toxins, immunologic mediators, antigens and pharmacologic mediators.

29. Method according to claim 17 wherein the predetermined protein is Interleukin-1.

30. Method according to claim 17 wherein the predetermined protein is tissue plasminogen activator.

31. Method according to claim 17 wherein the microbial host is selected from the group consisting of *B. subtilis* and *E. coli*.

32. Method according to claim 17 wherein the microbial host is *B. subtilis*.

33. Method according to claim 32 wherein the *B. subtilis* is double protease-minus.

34. Method according to claim 17 wherein the microbial host is *E. coli*.

* * * * *